United States Patent [19]

Simon et al.

[11] Patent Number: 5,480,396

[45] Date of Patent: Jan. 2, 1996

[54] LASER BEAM OPHTHALMOLOGICAL SURGERY METHOD AND APPARATUS

[76] Inventors: Gabriel Simon, Maestre Nicolau #23-6A, 08021 Barcelona, Spain; Cheng-Hao Huang, 8843 Larwin La., Orlando, Fla. 32817

[21] Appl. No.: 352,357

[22] Filed: Dec. 9, 1994

[51] Int. Cl.$^6$ .............................. A61N 5/06; A61B 17/36
[52] U.S. Cl. .................................. 606/4; 606/11
[58] Field of Search .................. 606/4, 5, 6, 10, 606/11, 12; 128/898

[56] References Cited

U.S. PATENT DOCUMENTS

| | | | |
|---|---|---|---|
| 3,621,181 | 11/1971 | Young | 219/121 L |
| 4,672,969 | 6/1987 | Dew | 128/397 |
| 4,812,613 | 5/1989 | Gorisch | 606/11 |
| 5,125,922 | 6/1992 | Dwyer et al. | 606/3 |
| 5,133,708 | 7/1992 | Smith | 606/5 |
| 5,139,494 | 8/1992 | Freiberg | 606/3 |
| 5,172,264 | 12/1992 | Morrow | 359/349 |
| 5,304,167 | 4/1994 | Freiberg | 606/3 |
| 5,312,396 | 5/1994 | Feld et al. | 606/11 |
| 5,325,393 | 6/1994 | Nighan, Jr. et al. | 372/97 |
| 5,411,502 | 5/1995 | Zair | 606/10 |
| 5,437,658 | 8/1995 | Muller et al. | 606/5 |

*Primary Examiner*—Stephen C. Pellegrino
*Assistant Examiner*—Sonya Harris-Ogugua
*Attorney, Agent, or Firm*—William M. Hobby, III

[57] ABSTRACT

A laser beam ophthalmological surgery method includes the steps of generating a laser beam and splitting the generated laser beam into multiple laser beams which are simultaneously focused onto a plurality of scanners. Each scanner in turn produces a predetermined scanning pattern focused on the cornea of a patient's eye to ablate the cornea tissue and with at least two beams simultaneously scanning and ablating the cornea tissue. Scanning is controlled from a central processing unit to perform the surgical procedure, removing a laser thickness of the cornea tissue to provide a safer and more predictable surgical procedure in the reshaping of the cornea. A laser ophthalmological surgery apparatus is provided which includes a laser generating a laser beam, a beam splitter for splitting the laser beam into a plurality of laser beams, and a plurality of scanners, each positioned for receiving one of the laser beams from the beam splitter and producing a predetermined scanning pattern from the laser beam and impinging the scanning pattern upon the cornea of a patient's eye.

18 Claims, 2 Drawing Sheets

LASER BEAM OPHTHALMOLOGICAL SURGERY METHOD AND APPARATUS

BACKGROUND OF THE INVENTION

This invention relates to refractive eye surgery and especially to refractive eye surgery using a plurality of laser beams in the ablation of cornea tissue to reshape the cornea of a person's or animal's eye.

The cornea is a thin shell with nearly concentric anterior and posterior surfaces and a central thickness of about 520 micrometers. It has an index of refraction of 1.377 and a nominal radius of curvature of 7.86 mm. The epithelium, forming the anterior surface of the cornea, is about 70 micrometers thick in young people at the center. Underlying the epithelium is a layer called Bowman's layer or Bowman's membrane, which is about 12 micrometers thick. This covers the anterior surface of the stroma, which makes up the bulk of the cornea and consists primarily of collagen fibers. The endothelium forms the posterior layer of the cornea and is a single layer of cells.

About three-quarters of the refractive power of the eye is determined by the curvature of the anterior surface of the cornea, so that changing the shape of the cornea offers a way to significantly reduce or eliminate a refractive error of the eye. The stroma is thick enough so that portions of its anterior region can be ablated away to change its profile and thus change the refractive power of the eye for corrective purposes, while leaving plenty of remaining stroma tissue.

Various lasers have been used for ophthalmic applications including the treatments of glaucoma, cataract and refractive surgery. For refractive surgeries (or corneal reshaping), ultraviolet (UV) lasers (excimer at 193 nm and fifth-harmonic of Nd:YAG at 213 nm) have been used for large area surface corneal ablation in a process called photorefractive keratectomy (PRK). Corneal reshaping may also be performed by laser thermal coagulation currently conducted with Ho:YAG lasers using a fiber-coupled, contact and non-contact type process.

Refractive surgery has reached a new dimension due to the development of the excimer laser (193 nm) and fifth harmonic of solid state laser (190 nm–215 nm) being used to photoablate the cornea tissue to reshape the cornea. Several approaches have been proposed to deliver the laser beams to the surface of the cornea including using a mask or diaphragm and move the mask or diaphragm to block the laser beam to achieve a desired curvature on the outer surface of the cornea. It has also been proposed to use a scanner to move a laser beam spot on the outer surface of the cornea to ablate the tissue to change the curvature on the cornea. Combining the mask or diaphragm and scanner to block and move a laser beam is also used to achieve a desired curvature on the outer surface of the cornea. The mask or diaphragm approach requires a high energy laser and a rough or stepped cornea surface is generated in the laser interacting with the cornea. When the laser interacts with the corneal tissue, it generates some water that remains on the surface of the cornea (like sweat water). This changes the ablation rate when a new laser pulse reaches the cornea. If this is not taken into consideration, an irregular pattern can be induced called an "island". Central corneal islands have been described in connection with prior laser beam delivery systems. The scanning or combination of mask and scanner approach produces a smoother cornea surface but nonsymmetrical beam profiles and the sweat water effect creates an island effect which is caused by a nonsymmetrical ablation on each side or point of the corneal surface. The present invention uses two or more laser beams which multiple laser beams are split from one laser source with an out of phase relationship. The spatial energy distribution mode is scanned on the cornea or in the cornea simultaneously by using two or more scanning devices controlled by a predetermined program in a computer controller. Because the symmetrical laser beams are located and moved on the cornea, the cornea will compensate for the uneven situation of the sweat water effect when the laser interact with the cornea tissue and non-symmetrical laser beam spatial energy distribution.

Refractive error can be divided in two categories. Spherical and cylindrical. Spherical can effect the eye as myopic or hyperopic. Cylindrical can effect the eye as myopic or hyperopic astigmatism. The present invention uses a computer program to avoid ablation of the central part of the cornea in the hyperopic astigmatism and thus results in a safer, more predictable, and faster surgery procedure.

In the case of hyperopic combined with astigmatism of any cornea, the center is never touched.

SUMMARY OF THE INVENTION

A laser beam ophthalmological surgery method includes the steps of generating a laser beam and splitting the generated laser beam into a plurality of laser beams which are simultaneously focused onto a plurality of scanners. Each scanner produces a predetermined laser beam scanning pattern and is directed onto the cornea of a patient's eye to ablate the cornea tissue and with at least two scanning beams simultaneously ablating the cornea tissue. Scanning is controlled from a central processing unit to perform the surgical procedure. A laser ophthalmological surgery apparatus is provided which includes a laser generating a laser beam, a beam splitter for splitting the laser beam into a plurality of laser beams. A plurality of scanners are each positioned for receiving one of the laser beams from the beam splitter and producing a predetermined scanning pattern from the laser beam and impinging the scanning pattern upon the cornea of a patient's eye. The apparatus also includes focusing optics for focusing each laser beam and optics for directing the scanned beams onto the cornea in a predetermined scanning pattern for ablating a portion of the cornea of the eye. A computer connected to each scanner produces the desired scanning pattern which may be either a concentrical circular symmetrical pattern or a linear parallel symmetrical beam pattern.

BRIEF DESCRIPTION OF THE DRAWINGS

Other objects, features, and advantages of the present invention will be apparent from the written description and the drawings in which.

DESCRIPTION OF THE PREFERRED EMBODIMENT

Figure 1:
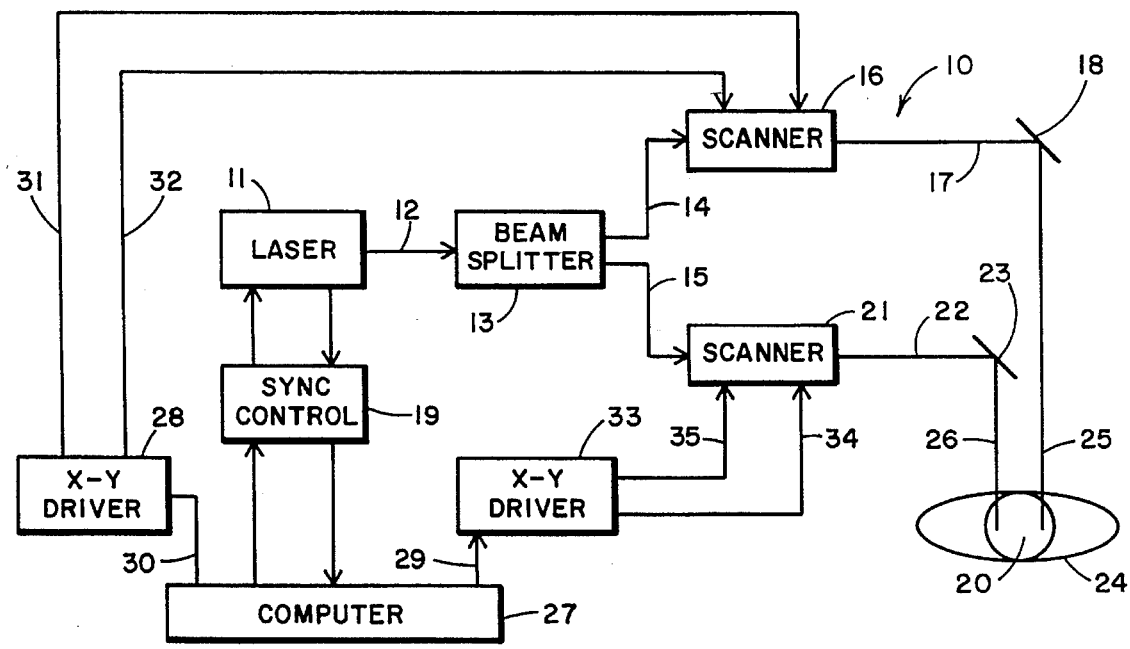
FIG. 1 is a block diagram of a dual laser beam cornea ablation system.

Referring to the drawings and especially to FIG. 1, a block diagram of a dual laser beam cornea ablation system 10 is shown having a laser 11 which can be an excimer laser producing a laser beam 12 having an ultraviolet wavelength of 193 nm. The laser beam 12 is impinged upon a beam splitter 13 which divides the beam 12 into two laser beams 14 and 15. Laser beam 14 is then impinged upon a galvanometer scanner 16 which is a typical scanner using a galvanometer having a mirror attached thereto in which the galvanometer produces a motion to thereby move the mirror having the beam 14 impinged thereupon to scan the beam. The scanning beam 17 is directed with mirrors 18 or other optics to apply the beam to a patient's cornea 20. The beam 15 is applied to a second scanner 21 producing a scanned beam 22 onto a mirror or other beam directing optics 23 onto the cornea 20 of a patient's eye 24. The beams 17 and 22, as directed by the optics 18 and 23, produce parallel laser beams 25 and 26 which simultaneously impinge upon the cornea 20 of the eye 24 and have a controlled pattern in accordance with the scanners 16 and 21.

In the present invention, a microcomputer 27 is connected to the laser 11 through the synchronization and every central circuit 19 and can be programmed to produce any type of scanning pattern desired and is connected to an X,Y coordinate scan driver 28 through the line 30 which produces X,Y coordinate scan driver signals in the lines 31 and 32 connected to the scanner 16 so that electrical signals from the X,Y coordinate scan driver 28 drive the scanner 16 in an X,Y coordinate pattern. The computer 27 puts out identical X,Y coordinate scan signals to the X,Y coordinate scan driver 33 through the connection 29 which in turn puts out X,Y coordinate signals in the lines 34 and 35 which are connected to the scanner 21 to produce an X,Y coordinate scanning pattern in the scanner 21. The scanning beams 25 and 26 impinging upon the eye in the case of an excimer laser has a beam wavelength of 193 nm but each beam may have an out of phase relationship with each other beam on the spatial energy distribution mode by using the transmittance and reflective characteristics of the beam splitter 13.

Figure 3:
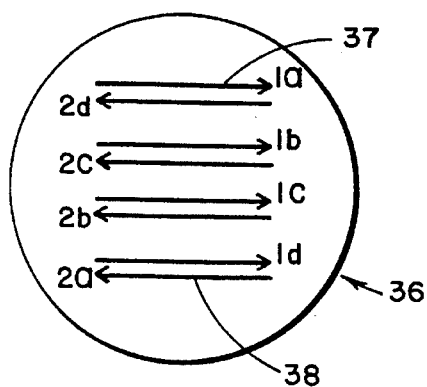
FIG. 3 is a scan pattern using the apparatus of FIGS. 1 and 2.
Figure 4:
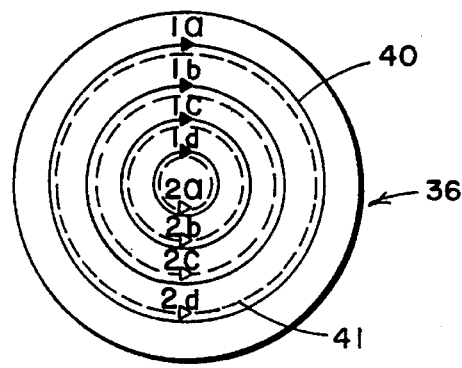
FIG. 4 is a second scan pattern which can be performed with the apparatus of FIGS. 1 and 2.
Figure 5:
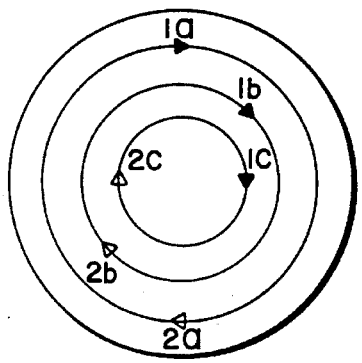
FIG. 5 is a diagrammatic scan pattern similar to FIG. 4 with a pair of laser beams scanning in a circular path and in the same direction of rotation.

The use of two or more scanning devices scanning two or more laser beams on the outer surface of the cornea is used to ablate the eye simultaneously with each beam. This can be accomplished in the patterns as shown in FIG. 3 in which the circle 36 indicates the cornea of the eye and the scan line 37 scanning in one direction is performed by one of the scanning laser beams 25 or 26 while the scanner 38 scans simultaneously in the opposite direction to the scanning beam 37 with both beams scanning simultaneously and superimposed trace. However as can be seen, the scanning lines are numbered 1a-1d and going in the opposite direction from the scans 2a-2d to indicate that, in the case of two laser beams 25, scanning line 37 is scanning in one direction while the laser beam 26 scans the lines 38 from the opposite side and in the opposite direction from the laser beam scan lines 37. Similarly as shown in FIG. 4, the cornea 36 is scanned in a circular fashion with a scan line 40 going in one direction while the laser beam 26 is scanned superimposed thereto along scan lines 41 from the opposite side of the eye 36 with both beams scanning simultaneously. Beam 26 is shown scanning with the dashed lines while solid lines are indicating the scanning of beam 25.

Figure 2:
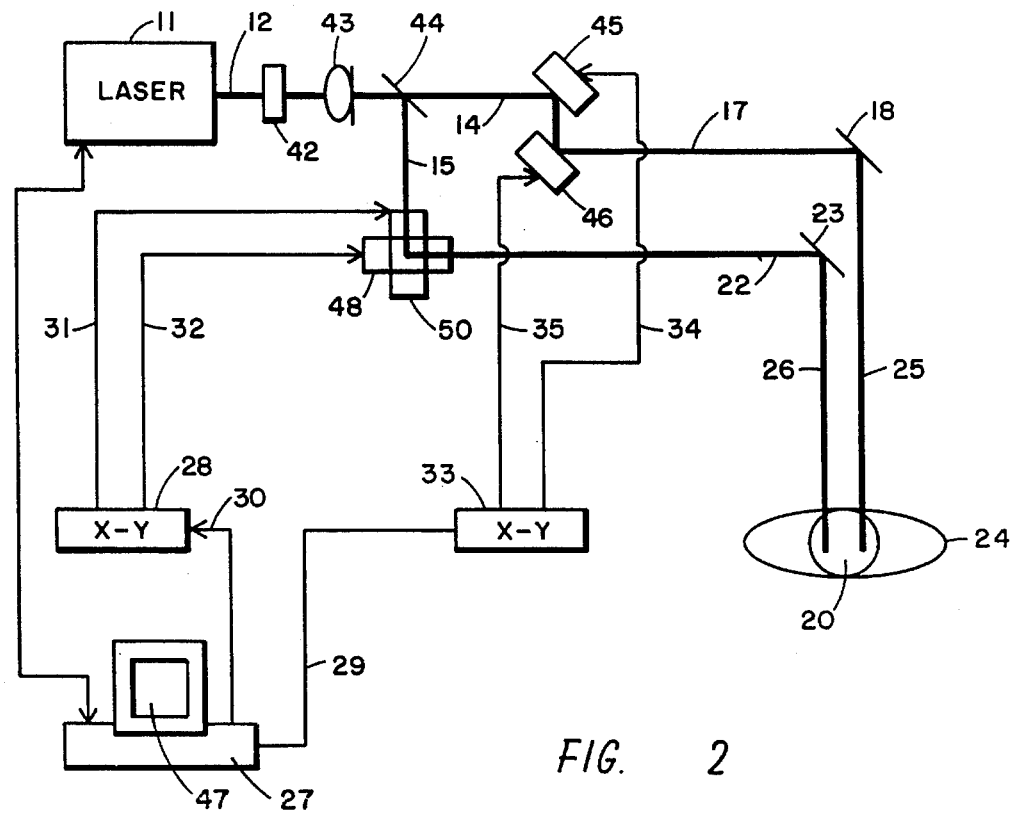
FIG. 2 is a schematic diagram of the optics for a dual laser beam cornea ablation system.

Referring more specifically to FIG. 2 of the drawings, the laser 11 which, again may be an excimer laser producing an ultraviolet output beam 12, is applied to a shutter 42 which in turn applies the laser beam to a focusing lens 43. The focusing lens focuses the beam 12 upon a beam splitter 44. The focusing lens 43 and beam splitter 44 are part of the focusing and beam splitter 13 of FIG. 1 and produce the split beams 14 and 15. It will, of course, be clear that the beam could be split into more than two beams as desired without departing from the spirit and scope of the invention. The beam 14 is then applied to the scanning pair 16 of FIG. 1 which has a first scanner 45 scanning the beam and applying the scanned beam to a second scanner 46. Both scanners 45 and 46 are galvanometer scanners having electrical galvanometers having mirrors attached thereto so that the scanner 45 can scan the beam in a Y direction while the scanner 46 can scan the beam in an X direction to give an X,Y control of the beam 17 being impinged upon the mirror 18 to form the scanning beam 25 onto the eye 24 cornea 20. The scanner 45 has a Y coordinate signal applied thereto through the line 34 while the scanner 46 has a line applied thereto through the X coordinate line 35, which signals are produced in the X,Y coordinate scan driver 33 which receives the control signals through the line 29 from the central processing unit 27. The computer 27 has a control screen 47 mounted thereto and also produces the X,Y coordinate control signals over the connection 30 to the X,Y coordinate scan driver 28 producing the Y coordinate signal through the connection 32 and the X coordinate signals through the connection 31 to a pair of scanners 48 and 50 which each produces one coordinate scanning signal which produces a scanning beam 22 controlled with optics 23 to form the eye scanning beam 26 onto the surface of the eye 24.

It should be clear at this time, that an apparatus has been provided for producing a plurality of laser beams which are simultaneously scanned over the surface of the cornea of the eye to ablate a portion of the eye for refractive correction to the cornea and which beams are produced simultaneously on opposite sides of a portion of the cornea and away from the center of the cornea for doing a controlled scan ablation of the cornea.

The method of performing laser beam ophthalmological surgery includes the step of generating a laser beam from a laser, then splitting the laser beam through a beam splitter 13 into a plurality of laser beams and then applying each split laser beam to an X,Y scanner or a pair of scanners which control the beam which scan beam is then applied through mirrors or optics onto the surface of the eye for performing the ablation of a portion of the cornea of the eye. Multiple scanning beams are scanned simultaneously and directed generally superimposed to each other in accordance with a computer program controlling the X,Y coordinate scanners controlling each of the pair of beam scanners for each of the laser beams. The process includes focusing the beams upon the beam splitter as well as directing the plurality of scanning laser beams onto the surface of the eye and in the controlling of the beams for predetermined patterns, such as illustrated in FIGS. 3 and 4.

Figure 6:
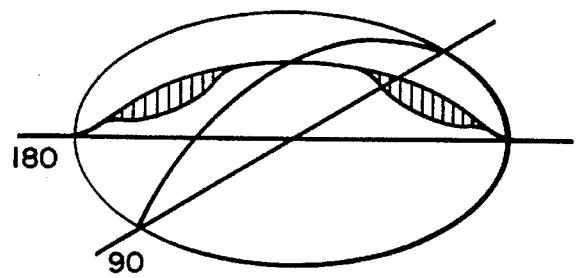
FIG. 6 is a cross-sectional view illustrating sculptured surface curvatures on both 90° and 180° for correcting hyperopic astigmatism.
Figure 8:
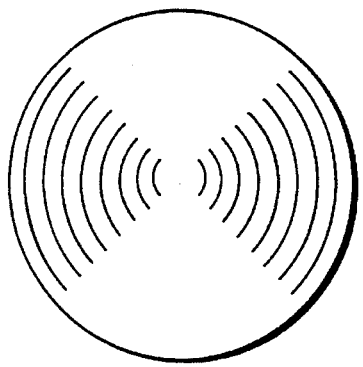
FIG. 8 is another pattern for correction of cornea astigmatic correction.
Figure 7:
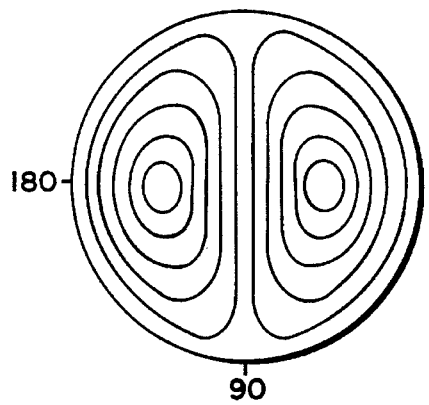
FIG. 7 illustrates one pattern for correction of cornea astigmatism correction.

FIG. 6 illustrates a typical cross-sectional view of a sculptured surface curvature of an eye on both 90° and 180° achieved with computer control for the hyperopic astigmatic correction while FIGS. 7 and 8 are algorithms of an ablated cornea for astigmatic correction, which corrections are performed in accordance with the present apparatus through the computer control of the computer 26.

In operation, the present multiple laser beam delivery system provides for the operator to make two computer selections. One selection is for myopic, hyperopic or astigmatism corrections which determines the dual beam scanners scanning pattern. Information is fed to the computer for issuing the necessary signals. The computer also has an input for the amount of dioptic correction for a particular patient's eye. The computer then puts out signals based on an algorithm for either myopic, hyperopic or astigmatism correction and for the dioptics of correction necessary for a particular patient's eye. The feedback signals from the scanner also allows the computer to make corrections in the driving of the multiple scanner pairs to manipulate the multiple laser beam simultaneously. Thus, the computer produces a scan to ablate the cornea with a pair of laser beams in accordance with the algorithm shown in FIGS. 7 and 8 for a hyperopic astigmatic correction with the amount of correction being determined by the diopter input.

It should be clear at this time, that the present invention is directed to both a method and an apparatus for use in ophthalmological surgery on the outer surface of the cornea or in the cornea to reduce astigmatism or myopic or hyperopic correction or combinations of myopic and astigmatisms or combinations of hyperopic and astigmatism corrections by using two or more laser beams simultaneously with the multiple laser beams formed from beam splitters from the same laser source with an out of phase relationship with each beam obtained through the beam splitter and which beams are scanned on predetermined computer controlled laser scanners to perform refractive surgery on a patient's eye. The ablation with a plurality of laser beams in accordance with the present invention produces a refractive correction in the eye symmetrically ablating the central part of the cornea tissue when correcting hyperopic astigmatism, thus resulting in a safer and more predictable surgical procedure to correct hyperopic astigmatism. However, the present invention should not be construed as limited to the forms shown which are to be considered illustrative rather than restrictive.

We claim:

1. A laser beam ophthalmological surgery method for ablating a portion of a cornea comprising the steps of:
   generating a laser beam;
   splitting the generated laser beam into a plurality of laser beams;
   focusing each of said plurality of laser beams onto a scanner;
   scanning each of said plurality of laser beams in a predetermined scanning pattern for ablation of the cornea of a patient's eye;
   directing said plurality of scanning laser beams parallel to each other directly onto the surface of the cornea of an eye of a patient with said plurality of scanning beams scanning a generally superimposed parallel pattern to each other; and
   controlling each said scanner from a central processing unit to thereby surgically reshape the cornea of the eye.

2. A laser beam ophthalmological surgery method in accordance with claim 1 in which the step of scanning a plurality of laser beams includes scanning each of two laser beams, each laser beam being out of phase with the other laser beam.

3. A laser beam ophthalmological surgery method in accordance with claim 2 in which the step of splitting the generated laser beam into a plurality of laser beams includes splitting the laser beam into two laser beams and impinging each laser beam onto a separate scanner.

4. A laser beam ophthalmological surgery method in accordance with claim 3 in which each scanning laser beam is scanning a generally parallel and spaced beam from the other laser beam with each parallel beam forming a superimposing pattern with a second parallel beam.

5. A laser beam ophthalmological surgery method in accordance with claim 4 in which the step of controlling said scanning includes controlling two scanners with the same central processing unit.

6. A laser beam ophthalmological surgery method in accordance with claim 5 in which the step of generating a laser beam includes generating a laser beam having a ultra-violet wavelength between 193 nm and 215 nm.

7. A laser beam ophthalmological surgery method in accordance with claim 6 in which the step of generating a laser beam includes generating a laser beam from an excimer laser having a wavelength of 193 nm.

8. A laser beam ophthalmological surgery method in accordance with claim 5 in which the step of scanning each of said laser beam includes scanning each laser beam with a pair of galvanometer scanners.

9. A laser beam ophthalmological surgery method in accordance with claim 8 in which the step of scanning each of said pair of scanning beams includes scanning each of said laser beams of the two beams in a plurality of generally straight lines, each parallel to the other and each beam traveling in an opposite direction from the other.

10. A laser beam ophthalmological surgery method in accordance with claim 9 in which the step of scanning a pair of laser beams includes scanning each of said laser beams of the two laser beams parallel to each other in a generally circular beam pattern around the central portion of the cornea.

11. A laser ophthalmological surgery apparatus for ablating a portion of a cornea comprising:
    a laser for generating a laser beam;
    a beam splitter for splitting the laser beam from said laser into a plurality of laser beams;
    a plurality of scanners, each positioned for receiving one of said laser beams from said beam splitter and producing a predetermined scanning pattern from the laser beam impinging thereupon;
    focusing optics positioned between said laser and said beam splitter for focusing each of said laser beams onto one said scanner;
    directing means positioned between said plurality of scanners and said cornea for directing each of said laser beams onto the cornea of a patient's eye simultaneously in a parallel pattern for ablating a portion of the cornea of the eye; and
    a computer connected to each said scanner for controlling each said scanner in a predetermined pattern whereby a plurality of laser beams can perform a surgical procedure on a patient's eye.

12. A laser beam ophthalmological surgery apparatus in accordance with claim 11 in which said beam splitter produces a plurality of out of phase laser beams.

13. A laser beam ophthalmological surgery apparatus in accordance with claim 12 in which said beam splitter splits the generated laser beam into two out of phase laser beams and each laser beam impinged onto a separate beam scanner.

14. A laser beam ophthalmological surgery apparatus in accordance with claim 13 in which said directing means directs each scanning laser beam generally parallel and spaced from each other onto a patient's eye.

15. A laser beam ophthalmological surgery apparatus in accordance with claim 14 in which said computer controls each of said beam scanners simultaneously.

16. A laser beam ophthalmological surgery apparatus in accordance with claim 15 in which said laser generates a laser beam having an ultra-violet wavelength between 193 nm and 215 nm.

17. A laser beam ophthalmological surgery apparatus in accordance with claim 16 in which said laser is an eximer laser having a wavelength of 193 nm.

18. A laser beam ophthalmological surgery apparatus in accordance with claim 17 in which each said scanner is a galvanometer scanner having a mirror mounted to galvanometer.

* * * * *